United States Patent
Muya et al.

(10) Patent No.: US 10,151,936 B2
(45) Date of Patent: *Dec. 11, 2018

(54) CONTACT LENS PACKAGING SOLUTIONS

(71) Applicant: Novartis AG, Basel (CH)

(72) Inventors: Leroy Wainaina Muya, Duluth, GA (US); Howard Allen Ketelson, Dallas, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/792,808

(22) Filed: Oct. 25, 2017

(65) Prior Publication Data

US 2018/0059436 A1    Mar. 1, 2018

Related U.S. Application Data

(63) Continuation of application No. 15/352,171, filed on Nov. 15, 2016, now Pat. No. 9,829,723.

(60) Provisional application No. 62/262,724, filed on Dec. 3, 2015.

(51) Int. Cl.
| | |
|---|---|
| *G02C 7/04* | (2006.01) |
| *A45C 11/00* | (2006.01) |
| *B65B 5/04* | (2006.01) |
| *B65B 55/06* | (2006.01) |
| *B65B 55/14* | (2006.01) |
| *B65D 81/22* | (2006.01) |
| *C08L 33/14* | (2006.01) |
| *C08L 39/06* | (2006.01) |
| *A61L 2/07* | (2006.01) |
| *A61L 12/04* | (2006.01) |
| *B29D 11/00* | (2006.01) |
| *B65B 25/00* | (2006.01) |
| *B65B 55/22* | (2006.01) |

(52) U.S. Cl.
CPC ............ *G02C 7/049* (2013.01); *A45C 11/005* (2013.01); *A61L 2/07* (2013.01); *A61L 12/04* (2013.01); *B29D 11/00067* (2013.01); *B65B 5/04* (2013.01); *B65B 25/008* (2013.01); *B65B 55/06* (2013.01); *B65B 55/14* (2013.01); *B65B 55/22* (2013.01); *B65D 81/22* (2013.01); *C08L 33/14* (2013.01); *C08L 39/06* (2013.01); *C08L 2201/54* (2013.01); *C08L 2203/02* (2013.01); *G02C 2202/16* (2013.01)

(58) Field of Classification Search
CPC . G02B 1/043; G02B 1/10; G02B 1/18; G02B 1/041; G02B 1/12; G02B 5/23; G02C 7/049; G02C 7/04; G02C 2202/16; G02C 2202/06; G02C 7/083; G02C 7/047; G02C 7/102; G02C 7/046; G02C 7/048; G02C 13/00; G02C 5/00; G02C 5/001; A61L 27/34; A61L 27/18; A61L 27/26; A61L 2430/16; A61L 27/50; A61L 2400/10; A61L 27/52; A61L 12/04; A61L 2300/452; A61L 2420/06; A61L 27/54; A61L 29/06; A61L 12/08; A61L 2300/802; A61L 27/14; A61L 2400/18; B29L 2011/0041; B29C 33/40; B29C 45/26; B29C 39/42; B29C 71/00; B29C 2035/0827; B29C 2045/0027; B29C 35/0805; B29C 39/006; B29C 39/02; B29C 39/10; B29C 45/0025; B29C 45/2708; B29C 65/48; B29C 66/9532; B29C 67/246
USPC ............ 351/159.33, 159.73, 159.02, 159.24, 351/159.04, 159.36, 159.61, 159.01, 351/159.03, 159.22, 178; 422/26–28; 53/425

See application file for complete search history.

(56) References Cited

U.S. PATENT DOCUMENTS

| | | | | |
|---|---|---|---|---|
| 9,829,723 B2 * | 11/2017 | Muya | ............... | G02C 7/049 |
| 2008/0015282 A1 * | 1/2008 | McCabe | ............ | A61L 27/18 |
| | | | | 523/107 |
| 2012/0220690 A1 * | 8/2012 | Liu | .............. | G02B 1/043 |
| | | | | 523/107 |

* cited by examiner

*Primary Examiner* — Thomas K Pham
*Assistant Examiner* — Sharrief Broome
(74) *Attorney, Agent, or Firm* — Jian Zhou

(57) ABSTRACT

The present invention relates to improved contact lens products which not only have an improved and sustainable wettability. The contact lens product of the invention comprises a soft hydrogel contact lens immersed and autoclaved in a packaging solution including a polyoxyethylene-polyoxybutylene block copolymer and a high molecular weight copolymer of N-vinylpyrrolidone and at least one amino-containing vinylic monomer. The present invention also provides methods for making contact lens products of the invention.

20 Claims, No Drawings

CONTACT LENS PACKAGING SOLUTIONS

This application is a continuation of application Ser. No. 15/352,171 filed 15 Nov. 2016, now U.S. Pat. No. 9,829,723, which claims the benefit under 35 USC § 119 (e) of U.S. provisional application No. 62/262,724 filed 3 Dec. 2015, incorporated by reference in its entirety.

The present invention relates to a packaging solution for autoclaving and storing contact lenses and to contact lenses which have been packaged and autoclaved in such a packaging solution and have an improved and sustainable wettability.

BACKGROUND OF THE INVENTION

Silicone hydrogel (SiHy) contact lenses are widely used for correcting many different types of vision deficiencies. They are made of a hydrated, crosslinked polymeric material that contains silicone and a certain amount of water within the lens polymer matrix at equilibrium.

Water in a SiHy contact lens can provide the desirable softness that enable a SiHy lens to be worn for sufficiently long periods of time and provides patients with the benefits including adequate initial comfort (i.e., immediately after lens insertion), relatively short period of adapting time required for a patient to become accustomed to them, and/or proper fit. Higher water content would be desirable for providing SiHy contact lenses with biocompatibility and comfort. But, there is a limit to the amount of water (believed to be 80%) that a SiHy contact lens can contain while still possessing sufficient mechanical strength and rigidity required for a contact lens, like conventional hydrogel contact lenses. Moreover, high water content could also have undesired consequences. For instance, oxygen permeability of a SiHy contact lens could be compromised by increasing water content. Further, high water content in a SiHy lens could result in greater in-eye dehydration and consequently dehydration-induced wearing discomfort, because a SiHy contact lens with a high water content could deplete the limited supply of tears (water) of the eye. It is believed that in-eye dehydration may be derived from evaporation (i.e., water loss) at the anterior surface of the contact lens and such water loss is primarily controlled by water diffusion through a lens from the posterior surface to the anterior surface, and that the rate of diffusion is closely proportional to the water content of the lens bulk material at equilibrium (L. Jones et al., Contact Lens & Anterior Eye 25 (2002) 147-156, herein incorporated by reference in its entirety).

Incorporation of silicone in a contact lens material also has undesirable effects on the biocompatibility of the contact lens, because silicone is hydrophobic and has great tendency to migrate onto the lens surface being exposed to air. As a result, a SiHy contact lens will generally require a surface modification process to eliminate or minimize the exposure of silicone of the contact lens and to maintain a hydrophilic surface, including, for example, various plasma treatments (e.g., Focus® Night & Day® and Air Optix® from Alcon; PureVision® from Bausch & Lomb; and PremiO™ from Menicon); internal wetting agents physically and/or chemically embedded in the SiHy polymer matrix (e.g., Acuvue® Oasys®, Acuvue® Advance® and Acuvue® TruEye™ from Johnson & Johnson; Biofinity® and Avaira™ from CooperVision). Although surface modification techniques used in the commercial SiHy lens production may provide fresh (unused) SiHy lenses with adequately hydrophilic surfaces, a SiHy lenses worn in the eye may have dry spots and/or hydrophobic surface areas created due to air exposure, shearing forces of the eyelids, silicone migration, and/or partial failure to prevent silicone from exposure. Those dry spots and/or hydrophobic surface areas are non-wettable and susceptible to adsorbing lipids or proteins from the ocular environment and may adhere to the eye, causing patient discomfort.

Therefore, there is still a need for cost-effective methods not only for improving the wettability of silicone hydrogel contact lenses but also for rendering such a wettability sustainable.

The following publications: U.S. Pat. Nos. 6,099,122, 6,367,929, 6,436,481, 6,440,571, 6,447,920, 6,451,871, 6,465,056, 6,500,481, 6,521,352, 6,586,038, 6,623,747, 6,630,243, 6,719,929, 6,730,366, 6,734,321, 6,793,973, 6,822,016, 6,835,410, 6,878,399, 6,884,457, 6,896,926, 6,923,978, 6,926,965, 6,940,580, 7,052,131, 7,249,848, U.S. Pat. Nos. 7,297,725, and 8,529,057; and U.S. Pat. Appl. Pub. Nos. US 2007/0229758A1, US 2008/0174035A1, and US 2008/0152800A1), US 2008/0226922 A1 and 2009/0186229 A1, US 2008/0142038A1, US 2009/0145086 A1, 2009/0145091A1, 2008/0142038A1, and 2007/0122540A1, disclose various surface modification methods for rendering silicone hydrogel contact lenses wettable.

The following publications: U.S. Pat. Nos. 5,882,687, 5,942,558, 6,348,507, 6,440,366, 6,531,432, 6,699,435, 8,647,658, and 8,689,971; and Published PCT Patent Applications WO9720019 and WO2006/088758, disclose that surfactants or lubricants are added in the lens packaging solution to ease to some extent initial discomfort and other symptoms.

SUMMARY OF THE INVENTION

The present invention, in one aspect, provides an ophthalmic product comprising a sealed and sterilized package which include a packaging solution and a soft hydrogel contact lens which has been immersed and autoclaved in the packaging solution, wherein the packaging solution is a buffered saline which includes a surfactant which is a poly(oxyethylene)-poly(oxybutylene) block copolymer and from about 0.1% to about 2% by weight of a lubricant which is a copolymer of N-vinylpyrrolidone and at least one amino-containing vinylic monomer, wherein the copolymer of N-vinylpyrrolidone and at least one amino-containing vinylic monomer has a molecular weight of at least 50,000 Daltons, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the packaging solution has a pH of from about 6.0 to about 8.0, an osmolality of from about 200 to about 450 mOsm/kg, and a viscosity of up to about 5.0 centipoises at 25° C., wherein the soft hydrogel contact lens has an improved and sustainable wettability.

The present invention, in another aspect, provides a process for making a soft contact lens having an improved and sustainable wettability. The method of the invention comprises the steps of: a) placing and sealing a hydrogel contact lens in a container containing a packaging solution, wherein the packaging solution is a buffered saline which includes a surfactant which is a poly(oxyethylene)-poly (oxybutylene) block copolymer and from about 0.1% to about 2% by weight of a lubricant which is a copolymer of N-vinylpyrrolidone and at least one amino-containing vinylic monomer, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the packaging solution has a pH of from about 6.0 to about 8.0, an osmolality of from about 200 to about 450 mOsm/kg, and a viscosity of up to about 5.0 centipoises at 25° C.; and b) autoclaving the sealed package containing the hydrogel contact lens therein for at least about 30 minutes to obtain the soft contact lens.

The present invention, in a further aspect, provides use of a packaging solution for imparting a hydrogel contact lens with an improved and sustainable wettability.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

"About" as used herein means that a number referred to as "about" comprises the recited number plus or minus 1-10% of that recited number.

In this application, the abbreviation "SiHy" means silicone hydrogel; the abbreviation "EO" means oxyethylene; the abbreviation "BO" means oxybutylene; the abbreviation "PEO-PBO-PEO" means poly(oxyethylene)-poly(oxybutylene)-poly(oxyethylene); the abbreviation "PEG" means polyethylene glycol.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a crosslinked polymeric material which is insoluble in water, but can absorb at least 10 percent by weight of water when it is fully hydrated.

A "silicone hydrogel" refers to a silicone-containing hydrogel obtained by copolymerization of a polymerizable composition comprising at least one silicone-containing vinylic monomer or at least one silicone-containing vinylic macromer or at least one actinically-crosslinkable silicone-containing prepolymer.

"Hydrophilic," as used herein, describes a material or portion thereof that will more readily associate with water than with lipids.

A "vinylic monomer" refers to a compound that has one sole ethylenically unsaturated group and is soluble in a solvent.

The term "olefinically unsaturated group" or "ethylenically unsaturated group" is employed herein in a broad sense and is intended to encompass any groups containing at least one >C=C<group. Exemplary ethylenically unsaturated groups include without limitation (meth)acryloyl

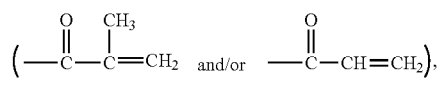

allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionizing radiation (e.g. gamma ray or X-ray irradiation), microwave irradiation, and the like. Thermal curing or actinic curing methods are well-known to a person skilled in the art.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

A "macromer" or "prepolymer" refers to a compound or polymer that contains ethylenically unsaturated groups and has an average molecular weights greater than 700 Daltons.

A "polymer" means a material formed by polymerizing/crosslinking one or more vinylic monomers, macromers and/or prepolymers.

"Molecular weight" of a polymeric material (including monomeric or macromeric materials), as used herein, refers to the number-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene" refers to a divalent radical obtained by removing one hydrogen atom from an alkyl. An alkylene group (or radical) forms two bonds with other groups in an organic compound.

In this application, the term "substituted" in reference to an alkylene divalent radical or an alkyl radical means that the alkylene divalent radical or the alkyl radical comprises at least one substituent which replaces one hydrogen atom of the alkylene or alkyl radical and is selected from the group consisting of hydroxyl, carboxyl, —NH$_2$, sulfhydryl, C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

As used herein, the term "multiple" refers to three or more.

A "vinylic crosslinker" refers to a compound having at least two ethylenically-unsaturated groups. A "vinylic crossliking agent" refers to a compound with two or more ethylenically unsaturated groups and with molecular weight less than 700 Daltons.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "polymerizable UV-absorbing agent" or "UV-absorbing vinylic monomer" refers to a compound comprising an ethylenically-unsaturated group and a UV-absorbing moiety.

A "UV-absorbing moiety" refers to an organic functional group which can absorb or screen out UV radiation in the range from 200 nm to 400 nm as understood by a person skilled in the art.

In accordance with the invention, a packaging solution is ophthalmic safe. The term "ophthalmically safe" with respect to a packaging solution is meant that a contact lens immersed in the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

A "leachable polymeric lubricant" as used herein refers to a non-ionic hydrophilic polymer which is not covalently bound to but instead is associated with or entrapped in the polymer matrix of a contact lens and which can enhance surface wettability of a contact lens and/or the eye or reduce the frictional character of the contact lens surface.

"Dye" means a substance that is soluble in a lens-forming fluid material and that is used to impart color. Dyes are typically translucent and absorb but do not scatter light.

A "pigment" means a powdered substance (particles) that is suspended in a lens-forming composition in which it is insoluble.

"Surface modification" or "surface treatment", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, a surface treatment by energy (e.g., a plasma, a static electrical charge, irradiation, or other energy source), chemical treatments, the grafting of hydrophilic vinylic monomers or macromers onto the surface of an article, mold-transfer coating process disclosed in U.S. Pat. No. 6,719,929 (herein incorporated by reference in its entirety), the incorporation of wetting agents into a lens formulation for making contact lenses proposed in U.S. Pat. Nos. 6,367,929 and 6,822,016 (herein incorporated by references in their entireties), reinforced mold-transfer coating disclosed in U.S. Pat. No. 7,858,000 (herein incorporated by reference in its entirety), and a hydrophilic coating composed of covalent attachment or physical deposition of one or more layers of one or more hydrophilic polymer onto the surface of a contact lens disclosed in U.S. Pat. Nos. 8,147,897 and 8,409,599 and US Patent Application Publication Nos. 2011/0134387, 2012/0026457 and 2013/0118127 (herein incorporated by references in their entireties).

"Post-curing surface treatment", in reference to a silicone hydrogel material or a soft contact lens, means a surface treatment process that is performed after the formation (curing) of the hydrogel material or the soft contact lens in a mold.

A "hydrophilic surface" in reference to a silicone hydrogel material or a contact lens means that the silicone hydrogel material or the contact lens has a surface hydrophilicity characterized by having an averaged water contact angle of about 90 degrees or less, preferably about 80 degrees or less, more preferably about 70 degrees or less, more preferably about 60 degrees or less.

In this application, the term "water contact angle" refers to an average water contact angle which is obtained by averaging measurements of at least 3 individual contact lenses according to Sessile Drop technique.

In this application, the term "improved wettability" in reference to a soft hydrogel contact lens, which has been immersed and autoclaved in a first packaging solution (i.e., a first buffered saline including a combination of a surfactant and a lubricant therein) in a sealed lens package, means that the hydrogel contact lens has a reduction-in-water-contact-angle, designated as $R_{WCA}$, of at least about 40% (preferably at least about 50%, more preferably at least about 60%, even more preferably at least about 70%, most preferably at least about 80%), wherein $$R_{WCA} = \frac{\overline{WCA_c} - \overline{WCA_t}}{\overline{WCA_c}} \times 100\%$$

in which $\overline{WCA_c}$ is the water contact angle of the control hydrogel contact lens immersed and autoclaved in the control (or second) buffered saline and $\overline{WCA_t}$ is the water contact angle of the hydrogel contact lens immersed and autoclaved in the first buffered saline. The procedures for determining $\overline{WCA_c}$ and $\overline{WCA_t}$ are described in Example 1.

In this application, the term "sustainable wettability" in reference to a hydrogel contact lens, which has been immersed and autoclaved in a first packaging solution (i.e., a first buffered saline including a combination of a surfactant and a lubricant therein) in a sealed lens package, means that the hydrogel contact lens has have a wearing-induced increase in water contact angle, designated "$\Delta \overline{WCA_{wearing}}$", of about 50% or less (preferably about 40% or less, more preferably about 30% or less, even more preferably about 20% or less) and optionally but preferably a blinking-induced increase in water contact angle, designated "$\Delta \overline{WCA_{Blinking}}$", of about 250% or less (preferably about 200% or less, more preferably about 150% or less, even more preferably about 100% or less) after 10 cycles of wetting/drying treatment, wherein $$\Delta \overline{WCA_{wearing}} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens which is measured directly out of the package without soaking in water or a buffered saline and $\overline{WCA_{16H}}$ is the water contact angle of the hydrogel contact lens which is measured after being transferred from the lens package to a container containing 1 mL of a phosphate buffered saline (pH=7.0 to 7.4) and then fully immersed and gently agitated in the phosphate buffered saline for 16 hours at 34° C., wherein $$\Delta \overline{WCA_{blinking}} = \frac{\overline{WCA_{10}} - \overline{WCA_0}}{\overline{WCA_0}}$$

in which $\overline{WCA_0}$ is the water contact angle of a hydrogel contact lens which is measured directly out of lens package, and $\overline{WCA_{10}}$ is the water contact angle of the hydrogel contact lens which is measured after 10 cycles of wetting/drying treatment. The procedures for determining $\overline{WCA_{16H}}$, $\overline{WCA_{OOP}}$, $\overline{WCA_0}$, and $\overline{WCA_{10}}$ are described in Example 1.

It is believed that a process, in which a hydrogel contact lens is transferred from the lens package to a container containing 1 mL of a phosphate buffered saline (pH=7.0 to 7.4) and then fully immersed and gently agitated in the phosphate buffered saline for 16 hours at 34° C., can be used as a model to approximately simulate a one-day of wearing of the hydrogel contact lens by a patient. $\overline{WCA_{16H}}$ can be a measure of the wettability of a hydrogel contact lens at the end-of-day (EOD) wearing. It is desirable that the wettability of a hydrogel contact lens would not deteriorate more than about 50% over a period of one-day wearing.

In this application, the term "10 cycles of wetting/drying treatment" refers to a system that consists of 3 test cycles and 7 non-test cycles. Each non-test cycle consisting of transferring each lens into a scintillation vial containing 10 mL of a borate-buffered saline (UNISOL®4) for 5 minutes, placing each lens onto a blotting paper for 1.5 minutes, and then transferring each lens to a new scintillation vial containing 10 mL of fresh borate-buffered saline (UNISOL®4). Each test cycle consists of placing each lens onto a blotting paper for 0.5 minute, placing the blotted lens on a sample holder and obtaining water contact angle measurements within 1 minute, and then followed by transferring each lens to a scintillation vial containing 10 mL of fresh borate-buffered saline (UNISOL®4). It is also believed that a 10 cycles of 5-minutes wetting and 1.5 minutes drying (air exposure) can be used to simulate the clinical contact lens wetting and drying conditions that occur during the normal blinking process.

The present invention is generally directed to a hydrogel contact lens capable of easing lens-wearer's initial discomfort. The present invention is partly based on the discovery that a lens packaging solution including a PEO-PBO block copolymer and a copolymer of N-vinylpyrrolidone and an amino-containing vinylic monomer can provide to a hydrogel contact lens (especially a silicone hydrogel contact lens), which has been immersed and autoclaved in the packaging solution, with unexpected benefits of increased and relatively-sustainable wettability and reduced friction.

Although the inventors do not wish to be bound by any particular theory, it is believed that a PEO-PBO block copolymer and a copolymer of N-vinylpyrrolidone and an amino-containing vinylic monomer can have synergetic effects on the wettability and lubricity of a hydrogel contact lens. They may form a relatively-stable film on a hydrogel contact lens which has been immersed and autoclaved in a buffered saline containing the PEO-PBO block copolymer and the copolymer of N-vinylpyrrolidone and an amino-containing vinylic monomer. Such a relatively-stable film on the hydrogel contact lens can greatly improve the wettability and lubricity, and is believed to allow the lens to settle gently on the eye with slight lubrication and improve initial insert comfort as well as improved wearing comfort until the end of day.

The present invention, in one aspect, provides an ophthalmic product comprising a sealed and sterilized package which include a first packaging solution and a soft hydrogel contact lens which has been immersed and autoclaved in the first packaging solution in the sealed package, wherein the first packaging solution is a first buffered saline which includes a surfactant which is a poly(oxyethylene)-poly(oxybutylene) block copolymer and from about 0.1% to about 2% by weight of a lubricant which is a copolymer of N-vinylpyrrolidone and at least one amino-containing vinylic monomer, wherein the copolymer of N-vinylpyrrolidone and at least one amino-containing vinylic monomer has a molecular weight of at least 50,000 Daltons, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the packaging solution has a pH of from about 6.0 to about 8.0, an osmolality of from about 200 to about 450 mOsm/kg, and a viscosity of up to about 5.0 centipoises at 25° C., wherein the soft hydrogel contact lens has a reduction-in-water-contact-angle, designated as $R_{WCA}$, of at least about 40% (preferably at least about 50%, more preferably at least about 60%, even more preferably at least about 70%, most preferably at least about 80%), wherein $$R_{WCA} = \frac{\overline{WCA_c} - \overline{WCA_t}}{\overline{WCA_c}} \times 100\%$$

in which $\overline{WCA_c}$ is the water contact angle of a control hydrogel contact lens immersed and autoclaved in a second buffered saline as control and $\overline{WCA_t}$ is the water contact angle of the hydrogel contact lens immersed and autoclaved in the first buffered saline, wherein the soft hydrogel contact lens has a sustainable wettability as characterized by have a wearing-induced increase in water contact angle, designated "$\Delta \overline{WCA_{wearing}}$", of about 50% or less (preferably about 40% or less, more preferably about 30% or less, even more preferably about 20% or less) and optionally but preferably a blinking-induced increase in water contact angle, designated "$\Delta \overline{WCA_{blinking}}$", of about 250% or less (preferably about 200% or less, more preferably about 150% or less, even more preferably about 100% or less), wherein $$\Delta \overline{WCA_{wearing}} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens and is measured directly out of the package and $\overline{WCA_{16H}}$ is the water contact angle of the hydrogel contact lens and is measured after being transferred from the package to a container containing 1 mL of a phosphate buffered saline (pH=7.0 to 7.4) and then fully immersed and gently agitated in the phosphate buffered saline for 16 hours at 34° C., wherein $$\Delta \overline{WCA_{blinking}} = \frac{\overline{WCA_{10}} - \overline{WCA_0}}{\overline{WCA_0}}$$

in which $\overline{WCA_0}$ is the water contact angle of the hydrogel contact lens which is measured directly out of the package, and $\overline{WCA_{10}}$ is the water contact angle of the hydrogel contact lens which is measured after 10-cycles of wetting/drying treatment.

Lens packages (or containers) are well known to a person skilled in the art for autoclaving and storing a soft hydrogel contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and autoclaved (i.e., heating under pressure to and at about 120° C. or higher) for at least 30 minutes prior to dispensing to users. A person skilled in the art will understand well how to seal and sterilize lens packages.

In accordance with the invention, a soft hydrogel contact lens can be a conventional hydrogel contact lens (i.e., a non-silicone hydrogel lens) or preferably a silicone hydrogel contact lens.

A packaging solution of the invention is ophthalmically compatible and may be any water-based solution that is used for the storage of contact lenses. A packaging solution of the invention can be a saline solution (i.e., an aqueous solution containing from about 0.15% to 0.95% by weight of one or more salts) or a buffered saline solution (i.e., a saline containing one or more buffering agents for maintaining the pH of the saline).

Examples of amino-containing vinylic monomers include without limitation alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, N-vinylalkylamide having 3-10 carbon atoms. Examples of preferred N-vinyl alkylamide include without limitation N-vinyl formaide, N-vinyl acetamide, N-vinyl isopropylamide, and N-vinyl-N-methyl acetamide.

Examples of preferred copolymers includes without limitation copolymers of N-vinyl pyrrolidone and dimethylaminoethylmethacrylate. Such preferred copolymers are commercially available, e.g., Copolymer 845 and Copolymer 937 from ISP.

In accordance with the invention, a poly(oxyethylene)-poly(oxybutylene) block copolymer must include a poly (oxyethylene) block as the hydrophilic component and a poly(oxybutylene) block as the hydrophobic component. It can be a di-block copolymer, denoted as PEO-PBO, a tri-block copolymer, represented as PEO-PBO-PEO or PBO-PEO-PBO, or other block-type configurations. Unless expressly indicated to the contrary, all references to "PEO-PBO block copolymers" herein include all of the foregoing forms. These copolymers may also be described in terms of the approximate or average value assigned to the respective repeating group. For example, $(EO)_{20}(BO)_5$, where the average value of the oxyethylene group is 20, and the average value of the oxybutylene group is 5.

Preferred polymers of the present invention are di-block copolymers of the following general formula:

wherein m is an integer having an average value of 10 to 1000 and n is an integer having an average value of 5 to 1000, provided that the value of m/n is from about 2:1 to about 10:1, preferably from about 3:1 to about 6:1.

PEO-PBO di-block copolymers of the following general formula are particularly preferred:

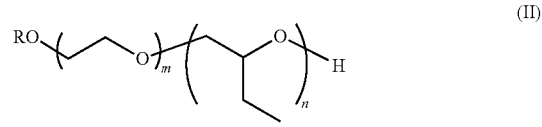

wherein R is selected from the group consisting of hydrogen, methyl, ethyl, propyl and butyl; m is an integer having an average value of 10 to 1000; and n is an integer having an average value of 5 to 1000, provided that the value of m/n is from about 2:1 to about 10:1, preferably from about 3:1 to about 6:1.

Most preferred is a copolymer of formula (II) wherein R is methyl; m has an average value of 45; and n has an average value of 10.

The PEO-PBO block copolymers utilized in the present invention have a molecular weight in the range of 1,000 to about 50,000 Daltons; and more preferably in the range of 2,000 to about 10,000 Daltons.

The PEO-PBO block copolymers described above may be synthesized according to procedures described in U.S. Pat. No. 8,318,144 (herein incorporated in reference in its entirety).

In a preferred embodiment of the invention, the packaging solution comprises from about 0.001% to about 1% by weight, preferably from about 0.005% to about 0.5% by weight, and more preferably from about 0.01% to 0.1% by weight of a PEO-PBO block copolymer.

The packaging solution of the present invention preferably contains a buffering agent for maintaining the pH the packaging solution in a physiologically acceptable range of about 6 to about 8. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino) ethanesulfonic acid), MOPS (3-[N-morpholino]-propanesulfonic acid), PIPES (piperazine-N,N'-bis(2-ethanesulfonic acid), TES (N-[Tris(hydroxymethyl)methyl]-2-aminoethanesulfonic acid), salts thereof, phosphate buffers (e.g. $Na_2HPO_4$, $NaH_2PO_4$, and $KH_2PO_4$) or mixtures thereof. Preferred buffering agents are borate buffers and phosphate buffers. The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

A packaging solution of the invention can optionally include a viscosity-enhancing polymers, which can be a water soluble cellulose-derived polymer, a water-soluble polyvinylalcohol (PVA), or combination thereof. Examples of useful cellulose-derived polymers include without limitation cellulose ethers. Exemplary preferred cellulose ethers are methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of preferably from about 0.1% to about 1% by weight, based on the total amount of the packaging solution.

In accordance with the invention, the solution can further comprises mucin-like materials, ophthalmically beneficial materials, and/or additional surfactants.

Exemplary mucin-like materials include without limitation polyglycolic acid and polylactides. A mucin-like material can be used as guest materials which can be released continuously and slowly over extended period of time to the ocular surface of the eye for treating dry eye syndrome. The mucin-like material preferably is present in effective amounts.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of preferred surfactants as additional surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of $C_{12}$-$C_{18}$ alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

A lens can be prepared according to any methods known to a person skilled in the art from a hydrogel lens-forming formulation. A "hydrogel lens-forming formulation" or "hydrogel lens-forming material" refers to a polymerizable composition which can be cured (i.e., polymerized and/or crosslinked) thermally or actinically to obtain a crosslinked/polymerized polymeric material. Lens-forming materials are well known to a person skilled in the art. Typically a lens forming material comprises polymerizable/crosslinkable components, for example, such as, monomers, macromers, prepolymers, or combinations thereof, as known to a person skilled in the art. A lens-forming material can further include other components, such as non-crosslinkable hydrophilic polymers (i.e., leachable polymeric lubricants), an initiator (e.g., a photoinitiator or a thermal initiator), a visibility tinting agent, UV-blocking agent, photosensitizers, antimicrobial agents (e.g., Ag-nanoparticles), and the like.

Examples of lens making include without limitation, cast-molding, spin-casting, and lathing. A person skilled in the art will know well how to cast-mold lenses from a lens-forming formulation in molds based on thermal or actinic polymerization.

For production of conventional hydrogel contact lenses, a hydrogel lens formulation typically is: either (1) a monomer mixture comprising (a) at least one hydrophilic vinylic monomer (e.g., hydroxyethyl methacrylate, glycerol methacrylate, N-vinylpyrrolidone, or combinations thereof) and (b) at least one component selected from the group consisting of a crosslinking agent, a hydrophobic vinylic monomer, a lubricating agent (or so-called internal wetting agents incorporated in a lens formulation), a free-radical initiator (photoinitiator or thermal initiator), a UV-absorbing agent, a visibility tinting agent (e.g., dyes, pigments, or mixtures thereof), antimicrobial agents (e.g., preferably silver nanoparticles), a bioactive agent, and combinations thereof; or (2) an aqueous solution comprising one or more water-soluble prepolymers and at least one component selected from the group consisting of hydrophilic vinylic monomer, a crosslinking agent, a hydrophobic vinylic monomer, a lubricating agent (or so-called internal wetting agents incorporated in a lens formulation), a free-radical initiator (photoinitiator or thermal initiator), a UV-absorbing agent, a visibility tinting agent (e.g., dyes, pigments, or mixtures thereof), antimicrobial agents (e.g., preferably silver nanoparticles), a bioactive agent, and combinations thereof. Resultant preformed hydrogel contact lenses then can be subjected to extraction with an extraction solvent to remove unpolymerized components from the resultant lenses and to hydration process, as known by a person skilled in the art. It is understood that a lubricating agent present in a hydrogel lens formulation can improve the lubricity of preformed hydrogel contact lenses compared to the lubricity of control preformed hydrogel contact lenses obtained from a control hydrogel lens formulation without the lubricating agent.

Examples of water-soluble prepolymers include without limitation: a water-soluble crosslinkable poly(vinyl alcohol) prepolymer described in U.S. Pat. Nos. 5,583,163 and 6,303,687; a water-soluble vinyl group-terminated polyurethane prepolymer described in U.S. Pat. No. 6,995,192; derivatives of a polyvinyl alcohol, polyethyleneimine or polyvinylamine, which are disclosed in U.S. Pat. No. 5,849,841; a water-soluble crosslinkable polyurea prepolymer described in U.S. Pat. Nos. 6,479,587 and 7,977,430; crosslinkable polyacrylamide; crosslinkable statistical copolymers of vinyl lactam, MMA and a comonomer, which are disclosed in U.S. Pat. No. 5,712,356; crosslinkable copolymers of vinyl lactam, vinyl acetate and vinyl alcohol, which are disclosed in U.S. Pat. No. 5,665,840; polyether-polyester copolymers with crosslinkable side chains which are disclosed in U.S. Pat. No. 6,492,478; branched polyalkylene glycol-urethane prepolymers disclosed in U.S. Pat. No. 6,165,408; polyalkylene glycol-tetra(meth)acrylate prepolymers disclosed in U.S. Pat. No. 6,221,303; crosslinkable polyallylamine gluconolactone prepolymers disclosed in U.S. Pat. No. 6,472,489; all of which are incorporated herein by references in their entireties.

For production of silicone hydrogel (SiHy) contact lenses, a SiHy lens formulation for cast-molding or spin-cast molding or for making SiHy rods used in lathe-cutting of contact lenses generally comprises at least one components selected from the group consisting of a silicone-containing vinylic monomer, a silicone-containing vinylic macromer, a silicone-containing prepolymer, a hydrophilic vinylic monomer, a hydrophobic vinylic monomer, a crosslinking agent (a compound having a molecular weight of about 700 Daltons or less and containing at least two ethylenically unsaturated groups), a free-radical initiator (photoinitiator or thermal initiator), a hydrophilic vinylic macromer/prepolymer, and combination thereof, as well known to a person skilled in the art. A SiHy contact lens formulation can also comprise other necessary components known to a person skilled in the art, such as, for example, a UV-absorbing agent, a visibility tinting agent (e.g., dyes, pigments, or mixtures thereof), antimicrobial agents (e.g., preferably silver nanoparticles), a bioactive agent, lubricating agents (or so-called internal wetting agents incorporated in a lens formulation), leachable tear-stabilizing agents, and mixtures thereof, as known to a person skilled in the art. Resultant preformed SiHy contact lenses then can be subjected to extraction with an extraction solvent to remove unpolymerized components from the resultant lenses and to hydration process, as known by a person skilled in the art. It is understood that a lubricating agent present in a SiHy lens formulation can improve the lubricity of preformed SiHy contact lenses compared to the lubricity of control preformed SiHy contact lenses obtained from a control SiHy lens formulation without the lubricating agent.

Numerous SiHy lens formulations have been described in numerous patents and patent applications published by the filing date of this application. All of them can be used in obtaining a preformed SiHy lens which in turn becomes the inner layer of a SiHy contact lens of the invention, so long as they will yield a SiHy material free of carboxyl group(s). A SiHy lens formulation for making commercial SiHy lenses, such as, lotrafilcon A, lotrafilcon B, balafilcon A, galyfilcon A, senofilcon A, narafilcon A, narafilcon B, comfilcon A, enfilcon A, asmofilcon A, somofilcon A, stenfilcon A, smafilcon A, enfilcon A, and efrofilcon A can also be used in making SiHy contact lenses.

In accordance with the present invention, a hydrogel or silicone hydrogel lens formulation (or a polymerizable fluid composition) can be a solution or a solvent-free liquid or melt at a temperature below 60° C.

In accordance with the invention, leachable lubricants are non-crosslinkable hydrophilic polymers (i.e. without anctinically-crosslinkable groups) having no charges. Any suitable non-charged hydrophilic polymers can be used so long as they are compatible with the lens-forming material (i.e., can produce optically clear contact lenses). Exemplary non-crosslinkable (i.e. without anctinically-crosslinkable groups) hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, alkylated polyvinylpyrrolidones, a homopolymer of acrylamide or methacrylamide, a copolymer of acrylamide or methacrylamide with one or more hydrophilic vinylic monomers, polyethylene oxide (PEO)), a polyoxyethylene derivative, poly-N—N-dimethylacrylamide, polyacrylic acid, poly 2 ethyl oxazoline, heparin polysaccharides, polysaccharides, and mixtures thereof. The number-average molecular weight $M_n$ of the hydrophilic polymer is preferably from 10,000 to 500,000, more preferably from 20,000 to 200,000.

Examples of polyvinylpyrrolidone (PVP) include without limitation those polymer characterized by molecular weight grades of K-15, K-30, K-60, K-90, K-120, and the likes.

Examples of copolymers of N-vinylpyrrolidone with one or more vinylic monomers includes without limitation N-vinylpyrrolidone/vinylacetate copolymers, N-vinylpyrrolidone/dimethylaminoethylmethacrylate copolymers (e.g., Copolymer 845, Copolymer 937, Copolymer 958 from ISP Corporation), N-vinylpyrrolidone/vinylcaprolactam/dimethylaminoethylmethacrylate copolymer.

Examples of alkylated pyrrolidones include without limitation the family of GANEX® Alkylated pyrrolidone from ISP Corporation.

A suitable polyoxyethylene derivative is, for example, n-alkylphenyl polyoxyethylene ether, n-alkyl polyoxy-ethylene ether (e.g., TRITON®), polyglycol ether surfactant (TERGITOL®), polyoxyethylenesorbitan (e.g., TWEEN®), polyoxyethylated glycol monoether (e.g., BRIJ®, polyoxylethylene 9 lauryl ether, polyoxylethylene 10 ether, polyoxylethylene 10 tridecyl ether), or a block copolymer of ethylene oxide and propylene oxide.

Examples of block copolymers of ethylene oxide and propylene oxide include without limitation poloxamers and poloxamines, which are available, for example, under the tradename PLURONIC®, PLURONIC-R®, TETRONIC®, TETRONIC-R® or PLURADOT®. Poloxamers are triblock copolymers with the structure PEO-PPO-PEO (where "PEO" is poly(ethylene oxide) and "PPO" is poly(propylene oxide).

A considerable number of poloxamers is known, differing merely in the molecular weight and in the PEO/PPO ratio; Examples of poloxamers include 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407. The order of polyoxyethylene and polyoxypropylene blocks can be reversed creating block copolymers with the structure PPO-PEO-PPO, which are known as PLURONIC-R® polymers.

Poloxamines are polymers with the structure (PEO-PPO)$_2$-N—(CH$_2$)$_2$—N-(PPO-PEO)$_2$ that are available with different molecular weights and PEO/PPO ratios. Again, the order of polyoxyethylene and polyoxypropylene blocks can be reversed creating block copolymers with the structure (PPO-PEO)$_2$-N—(CH$_2$)$_2$—N-(PEO-PPO)$_2$, which are known as TETRONIC-R® polymers.

Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available under the tradename PLURADOT®.

Non-crosslinkable PVAs of all kinds, for example those with low, medium or high polyvinyl acetate contents may be employed. In addition, the PVAs used may also comprise small proportions, for example up to 20%, preferably up to 5%, of copolymer units as mentioned before. The use of non-reactive PVAs with a content of polyvinyl acetate units of less than 20%, preferably lower than 16%, is preferred.

The non-crosslinkable polyvinyl alcohols employed in the present invention are known and are commercially available, for example under the brand name Mowiol® from KSE (Kuraray Specialties Europe).

It is understood that the addition of the leachable lubricants into the lens formulation should have no significantly adverse effects on the optical transparency of the resultant lenses. The leachable lubricants can be the same polymers having different molecular weights or different polymers having different molecular weights.

In a preferred embodiment, a soft hydrogel contact lens is a silicone hydrogel contact lens. More preferably, the silicone hydrogel contact lens has a plasma coating thereon.

In another preferred embodiment, a soft hydrogel contact lens is a silicone hydrogel contact lens and has at least one property selected from the group consisting of: an oxygen permeability of at least about 60 barrers (preferably at least about 70 barrers, more preferably at least about 80 barrers, even more preferably at least about 90 barrers); an elastic modulus of about 1.5 MPa or less (preferably about 1.2 MPa or less, more preferably about 1.0 or less, even more preferably from about 0.2 MPa to about 1.0 MPa); a water content of from about 15% to about 70% (preferably from about 20% to about 65%, more preferably from about 25% to about 60%, even more preferably from about 30% to about 55%) by weight when fully hydrated; a water contact angle of about 40 degrees or less (preferably about 30 degrees or less, more preferably about 20 degrees or less, even more preferably about 10 degrees or less); and combinations thereof.

In another preferred embodiment, a soft hydrogel contact lens of the invention has a coefficient of friction of about 0.6 or less (preferably about 0.5 or less, more preferably about 0.4 or less, even more preferably about 0.3 or less) as measured by AFM using a 5-micron SiO2 colloidal probe and the packaging solution as fluid lubricant (according to the procedures described in Example 2).

In another preferred embodiment, a soft hydrogel contact lens of the invention has a coefficient of friction of about 0.1 or less (preferably about 0.06 or less, more preferably about 0.02 or less, even more preferably about 0.09 or less) as measured by microtribometer using a 3.1 mm borosilcate glass sphere as probe and the packaging solution as fluid lubricant (according to the procedures described in Example 2).

The present invention, in another aspect, provides a process for making a soft contact lens having an improved and sustainable wettability. The method of the invention comprises the steps of: a) placing and sealing a hydrogel contact lens in a package containing a first packaging solution, wherein the first packaging solution is a first buffered saline which includes a surfactant which is a poly(oxyethylene)-poly(oxybutylene) block copolymer and from about 0.1% to about 2% by weight of a lubricant which is a copolymer of N-vinylpyrrolidone and at least one amino-containing vinylic monomer, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the packaging solution has a pH of from about 6.0 to about 8.0, an osmolality of from about 200 to about 450 mOsm/kg, and a viscosity of up to about 5.0 centipoises (preferably up to about 4.0 centipoises, even more preferably up to about 3.0 centipoises, most preferably from about 1.2 centipoises to about 2.5 centipoises) at 25° C.; and b) autoclaving the sealed package with the hydrogel contact lens therein for at least about 30 minutes to obtain the soft contact lens, wherein the soft hydrogel contact lens has a reduction-in-water-contact-angle, designated as $R_{WCA}$, of at least about 40% (preferably at least about 50%, more preferably at least about 60%, even more preferably at least about 70%, most preferably at least about 80%), wherein $$R_{WCA} = \frac{\overline{WCA_c} - \overline{WCA_t}}{\overline{WCA_c}} \times 100\%$$

in which $\overline{WCA_c}$ is the water contact angle of a control hydrogel contact lens immersed and autoclaved in a second buffered saline as control and $\overline{WCA_t}$ is the water contact angle of the hydrogel contact lens immersed and autoclaved in the first buffered saline, wherein the soft hydrogel contact lens has a sustainable wettability as characterized by have a wearing-induced increase in water contact angle, designated "$\Delta \overline{WCA}_{wearing}$", of about 50% or less (preferably about 40% or less, more preferably about 30% or less, even more preferably about 20% or less) and optionally but preferably a blinking-induced increase in water contact angle, designated "$\Delta \overline{WCA}_{blinking}$", of about 250% or less (preferably about 200% or less, more preferably about 150% or less, even more preferably about 100% or less), wherein $$\Delta \overline{WCA}_{wearing} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens and is measured directly out of the package and $\overline{WCA_{16H}}$ is the water contact angle of the hydrogel contact lens and is measured after being transferred from the package to a container containing 1 mL of a phosphate buffered saline (pH=7.0 to 7.4) and then fully immersed and gently agitated in the phosphate buffered saline for 16 hours at 34° C., wherein $$\Delta \overline{WCA}_{blinking} = \frac{\overline{WCA_{10}} - \overline{WCA_0}}{\overline{WCA_0}}$$

in which $\overline{WCA_0}$ is the water contact angle of the hydrogel contact lens which is measured directly out of the package, and $\overline{WCA_{10}}$ is the water contact angle of the hydrogel contact lens which is measured after 10-cycles of wetting/drying treatment.

Various embodiments and preferred embodiments of packaging solutions, soft hydrogel contact lenses, hydrogel lens-forming formulations (lens-forming materials), copolymers of vinylpyrolidone and at least one amino-containing vinylic monomer, amino-containing vinylic monomers, poly(oxyethylene)-poly(oxybutylene) block copolymers, the concentrations of poly(oxyethylene)-poly(oxybutylene) block copolymer, leachable lubricants, packages, buffering agents, additional components in the packaging solutions, sealing and sterilization, and the others are described above for the other aspect of the invention and can be used in this aspect of the invention.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. An ophthalmic product, comprising a sealed and sterilized package which includes a first packaging solution and a soft hydrogel contact lens which has been immersed and autoclaved in the first packaging solution in the sealed package,
    wherein the first packaging solution is a first buffered saline which includes a surfactant which is a poly(oxyethylene)-poly(oxybutylene) block copolymer and from about 0.1% to about 2% by weight of a lubricant which is a copolymer of N-vinylpyrrolidone and at least one amino-containing vinylic monomer, wherein the copolymer of N-vinylpyrrolidone and at least one amino-containing vinylic monomer has a molecular weight of at least 50,000 Daltons, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms,
    wherein the packaging solution has a pH of from about 6.0 to about 8.0, an osmolality of from about 200 to about 450 mOsm/kg, and a viscosity of up to about 5.0 centipoises at 25° C.,
    wherein the soft hydrogel contact lens has a reduction-in-water-contact-angle, designated as $R_{WCA}$, of at least about 40%, wherein $$R_{WCA} = \frac{\overline{WCA_c} - \overline{WCA_t}}{\overline{WCA_c}} \times 100\%$$

in which $\overline{WCA_c}$ is the water contact angle of a control hydrogel contact lens immersed and autoclaved in a second buffered saline as control and $\overline{WCA_t}$ is the water contact angle of the hydrogel contact lens immersed and autoclaved in the first buffered saline, wherein the soft hydrogel contact lens has a sustainable wettability as characterized by having a wearing-induced increase in water contact angle, designated "$\Delta\overline{WCA_{wearing}}$", of about 50% or less, wherein $$\Delta\overline{WCA_{wearing}} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens and is measured directly out of the package and $\overline{WCA_{16H}}$ is the water contact angle of the hydrogel contact lens and is measured after being transferred from the package to a container containing 1 mL of a phosphate buffered saline having a pH of 7.0 to 7.4 and then fully immersed and gently agitated in the phosphate buffered saline for 16 hours at 34° C.

2. The ophthalmic product of invention 1, wherein the soft hydrogel contact lens has a $R_{WCA}$ of at least about 50% (preferably at least about 60%, more preferably at least about 70%, even more preferably at least about 80%).

3. The ophthalmic product of invention 1 or 2, wherein the soft hydrogel contact lens has a $\Delta\overline{WCA_{wearing}}$ of about 40% or less (preferably about 30% or less, more preferably about 20% or less).

4. The ophthalmic product of any one of inventions 1 to 3, wherein the soft hydrogel contact lens has a sustainable wettability characterized by having a blinking-induced increase in water contact angle, designated "$\Delta\overline{WCA_{blinking}}$", of about 200% or less (preferably about 150% or less, more preferably about 100% or less), wherein $$\Delta\overline{WCA_{blinking}} = \frac{\overline{WCA_{10}} - \overline{WCA_0}}{\overline{WCA_0}}$$

in which $\overline{WCA_0}$ is the water contact angle of the hydrogel contact lens which is measured directly out of the package, and $\overline{WCA_{10}}$ is the water contact angle of the hydrogel contact lens which is measured after 10-cycles of wetting/drying treatment.

5. The ophthalmic product of any one of inventions 1 to 4, wherein the amino-containing vinylic monomer is dimethylaminoethylmethacrylate or dimethylaminoethylacrylate.

6. The ophthalmic product of any one of inventions 1 to 5, wherein the poly(oxyethylene)-poly(oxybutylene) block copolymer is a di-block copolymer of formula (I)

$$(EO)_m(BO)_n \qquad (I)$$

wherein m is an integer having an average value of 10 to 1000 and n is an integer having an average value of 5 to 1000, provided that the value of m/n is from about 2:1 to about 10:1.

7. The ophthalmic product of invention 6, wherein the value of m/n is from about 3:1 to about 6:1.

8. The ophthalmic product of invention 6 or 7, wherein the di-block copolymer has formula (II)

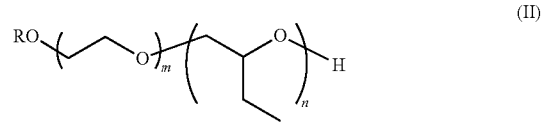

wherein R is selected from the group consisting of hydrogen, methyl, ethyl, propyl and butyl; m is an integer having an average value of 10 to 1000; and n is an integer having an average value of 5 to 1000, provided that the value of m/n is from about 2:1 to about 10:1.

9. The ophthalmic product of invention 8, wherein the value of m/n is from about 3:1 to about 6:1.

10. The ophthalmic product of invention 8, wherein in formula (II) R is methyl; m has an average value of 45; and n has an average value of 10.

11. The ophthalmic product of any one of inventions 1 to 10, wherein the packaging solution comprises from about 0.001% to about 1% by weight, preferably from about 0.005% to about 0.5% by weight, and more preferably from about 0.01% to 0.1% by weight of the poly(oxyethylene)-poly(oxybutylene) block copolymer.

12. The ophthalmic product of any one of inventions 1 to 11, wherein the hydrogel contact lens is a silicone hydrogel contact lens.
13. The ophthalmic product of invention 12, wherein the silicone hydrogel contact lens has a plasma coating thereon.
14. The ophthalmic product of invention 12 or 13, wherein the silicone hydrogel contact lens has at least one property selected from the group consisting of: an oxygen permeability of at least about 60 barrers; an elastic modulus of about 1.5 MPa or less; a water content of from about 15% to about 70% by weight when fully hydrated; a water contact angle of about 40 degrees or less; and combinations thereof.
15. The ophthalmic product of any one of inventions 12 to 14, wherein the silicone hydrogel contact lens has an oxygen permeability of at least about 60 barrers (preferably at least about 70 barrers, more preferably at least about 80 barrers, even more preferably at least about 90 barrers).
16. The ophthalmic product of any one of inventions 12 to 15, wherein the silicone hydrogel contact lens has an elastic modulus of about 1.5 MPa or less (preferably about 1.2 MPa or less, more preferably about 1.0 or less, even more preferably from about 0.2 MPa to about 1.0 MPa).
17. The ophthalmic product of any one of inventions 12 to 16, wherein the silicone hydrogel contact lens has a water content of from about 15% to about 70% (preferably from about 20% to about 65%, more preferably from about 25% to about 60%, even more preferably from about 30% to about 55%) by weight when fully hydrated.
18. The ophthalmic product of any one of inventions 12 to 17, wherein the silicone hydrogel contact lens has a water contact angle of about 40 degrees or less (preferably about 30 degrees or less, more preferably about 20 degrees or less, even more preferably about 10 degrees or less).
19. The ophthalmic product of any one of inventions 1 to 18, wherein the hydrogel contact lens includes one or more leachable lubricant therein.
20. A process for making a soft hydrogel contact lens, comprising the steps of:
    a) placing and sealing a hydrogel contact lens in a package containing a first packaging solution, wherein the first packaging solution is a first buffered saline which includes a surfactant which is a poly(oxyethylene)-poly(oxybutylene) block copolymer and from about 0.1% to about 2% by weight of a lubricant which is a copolymer of N-vinylpyrrolidone and at least one amino-containing vinylic monomer, wherein the copolymer of N-vinylpyrrolidone and at least one amino-containing vinylic monomer has a molecular weight of at least 50,000 Daltons, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the packaging solution has a pH of from about 6.0 to about 8.0, an osmolality of from about 200 to about 450 mOsm/kg, and a viscosity of up to about 5.0 centipoises (preferably up to about 4.0 centipoises, even more preferably up to about 3.0 centipoises, most preferably from about 1.2 centipoises to about 2.5 centipoises) at 25° C.; and
    b) autoclaving the sealed package with the hydrogel contact lens therein for at least about 30 minutes to obtain the soft contact lens,
    wherein the soft hydrogel contact lens has a reduction-in-water-contact-angle, designated as $R_{WCA}$, of at least about 40%, wherein $$R_{WCA} = \frac{\overline{WCA_c} - \overline{WCA_t}}{\overline{WCA_c}} \times 100\%$$

in which $\overline{WCA_c}$ is the water contact angle of a control hydrogel contact lens immersed and autoclaved in a second buffered saline as control and $\overline{WCA_t}$ is the water contact angle of the hydrogel contact lens immersed and autoclaved in the first buffered saline, wherein the soft hydrogel contact lens has a sustainable wettability as characterized by having a wearing-induced increase in water contact angle, designated "$\Delta\overline{WCA_{wearing}}$", of about 50% or less, wherein $$\Delta\overline{WCA_{wearing}} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens and is measured directly out of the package and $\overline{WCA_{16H}}$ is the water contact angle of the hydrogel contact lens and is measured after being transferred from the package to a container containing 1 mL of a phosphate buffered saline having a pH of 7.0 to 7.4 and then fully immersed and gently agitated in the phosphate buffered saline for 16 hours at 34° C.
21. The process of invention 20, wherein the soft hydrogel contact lens has a $R_{WCA}$ of at least about 50% (preferably at least about 60%, more preferably at least about 70%, most preferably at least about 80%).
22. The process of invention 20 or 21, wherein the soft hydrogel contact lens has a $\Delta\overline{WCA_{wearing}}$ of about 40% or less (preferably about 30% or less, more preferably about 20% or less).
23. The process of any one of inventions 20 to 22, wherein the soft hydrogel contact lens has a sustainable wettability characterized by having a blinking-induced increase in water contact angle, designated "$\Delta\overline{WCA_{blinking}}$", of about 250% or less (preferably about 200% or less, more preferably about 150% or less, even more preferably about 100% or less), wherein $$\Delta\overline{WCA_{blinking}} = \frac{\overline{WCA_{10}} - \overline{WCA_0}}{\overline{WCA_0}}$$

in which $\overline{WCA_0}$ is the water contact angle of the hydrogel contact lens which is measured directly out of the package, and $\overline{WCA_{10}}$ is the water contact angle of the hydrogel contact lens which is measured after 10-cycles of wetting/drying treatment.
24. The process of any one of inventions 20 to 23, wherein the amino-containing vinylic monomer is dimethylaminoethylmethacrylate or dimethylaminoethylacrylate.
25. The process of any one of inventions 20 to 24, wherein the poly(oxyethylene)-poly(oxybutylene) block copolymer is a di-block copolymer of formula (I)

$$(EO)_m(BO)_n \tag{I}$$

wherein m is an integer having an average value of 10 to 1000 and n is an integer having an average value of 5 to 1000, provided that the value of m/n is from about 2:1 to about 10:1.

26. The process of invention 25, wherein the value of m/n is from about 3:1 to about 6:1.

27. The process of invention 25 or 26, wherein the di-block copolymer has formula (II)

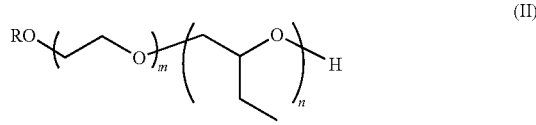

(II)

wherein R is selected from the group consisting of hydrogen, methyl, ethyl, propyl and butyl; m is an integer having an average value of 10 to 1000; and n is an integer having an average value of 5 to 1000, provided that the value of m/n is from about 2:1 to about 10:1.

28. The process of invention 27, wherein the value of m/n is from about 3:1 to about 6:1.

29. The process of invention 27, wherein in formula (II) R is methyl; m has an average value of 45; and n has an average value of 10.

30. The process of any one of inventions 20 to 29, wherein the packaging solution comprises from about 0.001% to about 1% by weight, preferably from about 0.005% to about 0.5% by weight, and more preferably from about 0.01% to 0.1% by weight of the poly(oxyethylene)-poly(oxybutylene) block copolymer.

31. The process of any one of inventions 20 to 30, wherein the hydrogel contact lens is a silicone hydrogel contact lens.

32. The process of invention 31, wherein the silicone hydrogel contact lens has a plasma coating thereon.

33. The process of invention 31 or 32, wherein the silicone hydrogel contact lens has at least one property selected from the group consisting of: an oxygen permeability of at least about 60 barrers; an elastic modulus of about 1.5 MPa or less; a water content of from about 15% to about 70% by weight when fully hydrated; a water contact angle of about 40 degrees or less; and combinations thereof.

34. The process of any one of inventions 31 to 33, wherein the silicone hydrogel contact lens has an oxygen permeability of at least about 60 barrers (preferably at least about 70 barrers, more preferably at least about 80 barrers, even more preferably at least about 90 barrers).

35. The process of any one of inventions 31 to 34, wherein the silicone hydrogel contact lens has an elastic modulus of about 1.5 MPa or less (preferably about 1.2 MPa or less, more preferably about 1.0 or less, even more preferably from about 0.2 MPa to about 1.0 MPa).

36. The process of any one of inventions 31 to 35, wherein the silicone hydrogel contact lens has a water content of from about 15% to about 70% (preferably from about 20% to about 65%, more preferably from about 25% to about 60%, even more preferably from about 30% to about 55%) by weight when fully hydrated.

37. The process of any one of inventions 31 to 36, wherein the silicone hydrogel contact lens has a water contact angle of about 40 degrees or less (preferably about 30 degrees or less, more preferably about 20 degrees or less, even more preferably about 10 degrees or less).

38. The process of any one of inventions 20 to 37, wherein the hydrogel contact lens includes one or more leachable lubricant therein.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

EXAMPLE 1

Surface Wettability Tests.

Water contact angle (WCA) on a contact lens is a general measure of the surface wettability of a contact lens. In particular, a low water contact angle corresponds to more wettable surface. Average contact angles (Sessile Drop) of contact lenses are measured using a VCA 2500 XE contact angle measurement device from AST, Inc., located in Boston, Mass. This equipment is capable of measuring advancing contact angles ($\theta_a$) or receding contact angles ($\theta_r$) or sessile (static) contact angles. Unless specified, water contact angle is sessile (static) contact angle. The measurements are performed on fully hydrated contact lenses and immediately after blot-drying. The blot-dried lens is then mounted on the contact angle measurement pedestal, and the sessile drop contact angle is automatically measured using the software provided by the manufacturer. The DI water used for measuring the contact angle has a resistivity >18MΩcm and the droplet volume used is 2 μl. The tweezers and the pedestal are washed well with Isopropanol and rinsed with DI water before coming in contact with the contact lenses.

Sustainable Wettability as Measured According to Simulated EOD Wearing Protocol

Lenses are removed from blister packages using a pair of tweezers and placed on a blotting material (e.g., a lint-free clean cloth, such as, Alpha Wipe TX1009) for 45 seconds on the front curve. Lenses are then inverted and placed on the blotting material for ~45 seconds prior to contact angle measurements being obtained on the front curve surface (a total of 90 seconds of contact lens exposure to air) according to the procedures described above. The obtained water contact angles are averaged and the averaged water contact angle measurements are $\overline{WCA_{OOP}}$.

Each lens is then transferred individually to a 24-well polystyrene plate containing 1 mL of a phosphate buffered saline (PBS, pH~7.0 to 7.4) per well equilibrated at 34° C. Lenses are gently agitated on a plate shaker at 34° C. in an incubator for 16 hours. After the 16 hours of incubation, the lenses are removed from the incubator and placed on a blotting material (e.g., a lint-free clean cloth, such as, Alpha Wipe TX1009) for 45 seconds on the front curve. Lenses are then inverted and placed on the blotting material for ~45 seconds prior to contact angle measurements being obtained on the front curve surface (a total of 90 seconds of contact lens exposure to air) according to the procedures described above. The obtained water contact angles are averaged and the averaged water contact angle is $\overline{WCA_{16H}}$.

Sustainable Wettability as Measured According to Simulated Blinking Protocol

The 10 cycles of wetting/drying treatment is a system that simulates contact lens wetting and drying conditions that occur during the normal blinking process and consists of 3 test cycles ($3^{rd}$, $5^{th}$, and $10^{th}$) and 7 non-test cycles ($1^{st}$, $2^{nd}$, $4^{th}$, $6^{th}$, $7^{th}$, $8^{th}$ and $9^{th}$). Each non-test cycle consisting of transferring each lens into a scintillation vial containing 10 mL of a borate-buffered saline (UNISOL®4) for 5 minutes, placing each lens onto a blotting paper for 1.5 minutes, and then transferring each lens to a new scintillation vial containing 10 mL of fresh borate-buffered saline (UNISOL®4). Each test cycle consists of placing each lens onto a blotting paper for 0.5 minute, placing the blotted lens on a sample holder and obtaining water contact angle measurements on the front curve surface within 1 minute according to the procedures described above, and then followed by transferring each lens to a scintillation vial containing 10 mL of fresh borate-buffered saline (UNISOL®4). The obtained water contact angles are averaged and the averaged water contact angle obtained at $10^{th}$ cycle is $\overline{WCA_{10}}$.

$\overline{WCA_0}$ is measured directly out of lens package as follows. Lenses are removed from blister packages using a pair of tweezers and placed on a blotting material (e.g., a lint-free clean cloth, such as, Alpha Wipe TX1009) for 30 seconds on the front curve. Contact angle measurements are obtained within next 60 seconds on the front curve surface according to the procedures described above. A total of 90 seconds of contact lens exposure to air. The obtained water contact angles are averaged and the averaged water contact angle is $\overline{WCA_0}$. After the measurements of $\overline{WCA_0}$, each lens is transferring to a scintillation vial containing 10 mL of fresh Unisol 4 solution, initiating the $1^{st}$ cycle.

Improved Wettability

Lenses are removed from blister packages using a pair of tweezers and placed on a blotting material (e.g., a lint-free clean cloth, such as, Alpha Wipe TX1009), dabbed well to remove surface water, mounted on the contact angle measurement pedestal, blown dry with a blast of dry air, and contact angle measurements are carried out on the front curve surface. The obtained water contact angles are averaged and the averaged water contact angle is $\overline{WCA_c}$ if the package solution contained in the blister packages is a control packaging solution or $\overline{WCA_t}$ if the package solution contained in the blister packages is a packaging solution under test (i.e., comprising a PEO-PBO block copolymer and a copolymer of N-vinylpyrrolidone and at least one amino-containing vinylic monomer).

EXAMPLE 2

Coefficient of Friction Measured with AFM Using a Colloidal Probe

Five spots on five distinct lenses from each lens packaging solution are measured. If friction forces between the silica probe and the lens surface are beneath the noise threshold (noise threshold directly related to the lateral stiffness of the AFM cantilever), then those data sets are not used in the calculation of the reported average friction coefficients. Lenses are removed from blister packages, mounted on a 8 mm base curve pedestal, and tested in the packaging solution at room temperature (RT). When finished, lenses are stored in the packaging solution.

F-D plots and a thermal method are used to calculate normal spring constant. The Sader method is employed to find the lateral spring constant. Friction plots on plasma cleaned silicon are used to calculate lateral sensitivity. The cantilever assembly used is described as follows: 5 micron $SiO_2$ colloidal probe, Novascan rectangular cantilever made of non-coated $SiO_2$; $K_{Normal}$=0.531 N/m; $K_{Lateral}$=107 N/m; Lateral Sensitivity=63 nN/V.

Friction vs. load plots are measured according to procedures previously described by Huo et al. in *Trib. Lett.* (2012) 45:505-513 (herein incorporated by reference in its entirety and fit to at least 50 nN of force due to the data being near noise level of machine at lower levels. Scans ranges from 50 nN up to 120 nN. Maximum deflection is taken to be 1V for all lenses.

Coefficient of Friction measured with Microtribometer

Microtribological experiments are performed using a custom built microtribometer previously described by Dunn et al. in *Tribol. Lett.* (2013) 49: 371-378 and by Urueña et al. in *Tribol. Lett.* (2015) 57: 9, both of which are incorporated by references in their entireties. A borosilicate glass probe (3.1 mm radius of curvature) is slid against an out-of-pack contact lens which is mounted to a horizontal, linearly reciprocating, piezoelectric stage. The contact lens holder is filled with 3 mL of a packing solution maintained at 34±4° C. that completely submerges the sample and the hemispherical probe during tribological measurements. The glass probe is mounted to a dual titanium flexure cantilever with normal and tangential force constants of 160 µN/µm and 75 µN/µm, respectively. Forces resulting from interactions of the sample and the probe are measured through normal and lateral capacitive displacement sensors mounted normal to and tangential to the cantilever assembly. The probe is lowered into the contact lens packing solution by a coarse positioning vertical micrometer stage. The measured cantilever displacements due to buoyancy forces resulting from submerging the probe are reinitialized prior to sliding. A vertical piezoelectric stage controls the initial approach of the glass probe onto the surface of the sample. This stage is used to apply monotonically increasing normal loads from ~100 to 2000 µN, with at least 20 reciprocating cycles between each increase in normal load. The reciprocating stroke length is 600 µm and the sliding velocity was 200 µm/s. Each reciprocating cycle generated a friction force loop consisting of 400 data points. The middle 20% of the friction force loop is analyzed to calculate the average friction force for each cycle [Equation 1].

$$\mu = \frac{F_{f,fwd} - F_{f,rev}}{2F_n} \quad (1)$$

The average normal load for each cycle is calculated over the middle 20% of the reciprocating loop. The largest source of normal load uncertainty originates from misalignments in the contact geometry. Ten cycles are averaged for each steady state normal force. The friction coefficient is determined by taking the slope of the curve obtained by fitting friction force vs. normal force data and their corresponding uncertainties using a Monte Carlo simulation [4]. For the microtribometer experiment, a single location on three of each lens type is evaluated. The borosilicate probe undergoes a solvent (methanol/ethanol) wipe between lens measurements.

EXAMPLE 3

Unless otherwise stated, all chemicals are used as received.

Synthesis of Macromer 51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the α,ω-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g).

13.78 g (88.9 mmol) of 2-isocyanatoethyl methacrylate (IEM) are added under argon to 247 g of the α,σ-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

Lens Preparation

A lens formulation is prepared as follows. 26 g of the macromer prepared above are added to a clean container. 19 g of 3-tris(trimethylsiloxy)silylpropyl methacrylate (TRIS from Shin-Etsu, product No. KF-2801) are added, followed by 1.00 gm of photoinitiator Darocur® 1173 (Ciba). 28.88 g dimethylacrylamide (DMA) are added, followed by 24.95 g of ethanol and appropriate amount of copper phthalocyanine (CuP) pigment stock dispersion in Tris to have 50 ppm of CuP in the lens formulation. After complete homogenization of the solution, this solution is filtered through a Teflon membrane having a pore width of 0.5 microns under nitrogen or air pressure. This solution is then pipetted into dust-free contact-lens moulds made from polypropylene. The molds are closed, and the polymerization reaction is effected by UV irradiation (5.0 mW/cm2, 30 min.), with simultaneous crosslinking. The molds are then opened in hot water. Lenses are removed from the open molds and extracted for 4 hours minimum with 100% isopropyl alcohol before being placed into water. The extracted lenses are subjected to plasma treatment according to procedures described in published US patent application No. 2002/0025389 to obtain plasma coatings. The plasma coated lenses are hydrated and finally equilibrated in a packaging solution in polypropylene blister packages and then autoclaved at 120° C. for 30 minutes.

EXAMPLE 4

Preparations of Packaging Solutions

Copolymer 845 is a copolymer of N-vinylpyrolidone and dimethylaminoethyl methacrylate and is obtained from ISP.

A PEO-PBO block copolymer of formula (II), in which R is methyl, m has an average value of 45; and n has an average value of 10, is prepared according to the procedures described in U.S. Pat. No. 8,318,144 (herein incorporated by reference in its entirety).

Four packaging solutions are prepared by dissolving various components in 1 L of water as shown in Table 1. The concentrations are weight percent.

TABLE 1

|  | I | II | III | IV |
|---|---|---|---|---|
| NaCl (% by weight) | 0.785 | 0.65 | 0.56 | 0.41 |
| $NaH_2PO_4 \cdot H_2O$ (% by weight) | 0.077 | 0.77 | 0.77 | 0.77 |
| $Na_2HPO_4 \cdot 7H_2O$ (% by weight) | 0.476 | 0.48 | 0.48 | 0.48 |
| Copolymer 845 (% by weight) |  | 1.0 |  | 1.0 |
| $CH_3O(EO)_{45}(BO)_{10}$ |  |  | 0.04 | 0.04 |

EXAMPLE 5

Lens Packaging

Plasma-coated lenses prepared in Example 3 are hydrated in water and packaged in blister packages containing a packaging solution (one of Packaging solutions II or IV prepared in Example 4), sealed and autoclaved according to the procedures described in Example 3.

Characterization of Sustainable Wettability

The packaged contact lenses prepared above in this Example, Biofinity® (CooperVision), ULTRA™ (Bausch & Lomb), PUREVISION® 2 (Bausch & Lomb), ACUVUE OASYS® (Johnson & Johnson) are tested for sustainable wettability according to the Simulated EOD Wearing Protocol described in Example 1.

The results are shown in Table 2.

TABLE 2

|  | $\overline{WCA_{OOP}}$ (°) | $\overline{WCA_{16H}}$ (°) | $\Delta WCA_{wearing}$ |
|---|---|---|---|
| Lenses packaged/autoclave in packaging sol. II | 7.1 ± 0.9 | 21.2 ± 2.4 | 199% |
| Lenses packaged/autoclave in packaging sol. IV | 7.4 ± 2.1 | 8.2 ± 1.4 | 11% |
| Biofinity | 15.0 ± 2.4 | 32.2 ± 2.2 | 115% |
| Ultra | 4.6 ± 0.4 | 5.7 ± 1.7 | 24% |
| Purevision2 | 36.0 ± 9.3 | 78.2 ± 8.9 | 117% |
| Acuvue Oasys | 6.5 ± 1.9 | 47.2 ± 10.8 | 626% |

EXAMPLE 6

Lens Packaging

Plasma-coated lenses prepared in Example 3 are hydrated in water and packaged in blister packages containing a packaging solution (one of Packaging solutions II or IV prepared in Example 4), sealed and autoclaved according to the procedures described in Example 3.

Characterization of Sustainable Wettability

The packaged contact lenses prepared above in this Example are tested for sustainable wettability according to the Simulated Blinking Protocol described in Example 1.

The results are shown in Table 3.

TABLE 3

| | $\overline{WCA_0}$ (°) | $\overline{WCA_{10}}$ (°) | $\Delta \overline{WCA_{Blinking}}$ |
|---|---|---|---|
| Lenses packaged/autoclave in packaging sol. II | 6 ± 1 | 35° ± 9 | 483% |
| Lenses packaged/autoclave in packaging sol. IV | 6 ± 2 | 13° ± 9 | 117% |

EXAMPLE 7

Lens Packaging

Plasma-coated lenses prepared in Example 3 are hydrated in water and packaged in blister packages containing a packaging solution (one of Packaging solutions I to IV prepared in Example 4), sealed and autoclaved according to the procedures described in Example 3.

Characterization of Sustainable Wettability

The packaged contact lenses prepared above in this Example are tested for lubricity according to the procedures described in Example 2.

The coefficients of friction measured with AFM are shown in Table 4.

TABLE 4

| | Coefficient of Friction | |
|---|---|---|
| | AFM | Microtribometer |
| Lenses packaged/autoclave in packaging sol. I | 1.12 ± 0.36 | 1.6100 ± 0.0460 |
| Lenses packaged/autoclave in packaging sol. II | 0.258 ± 0.095 | 0.0110 ± 0.0005 |
| Lenses packaged/autoclave in packaging sol. III | 0.255 ± 0.100 | 0.0060 ± 0.0004 |
| Lenses packaged/autoclave in packaging sol. IV | 0.274 ± 0.090 | 0.0270 ± 0.0020 |

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

The invention claimed is:

1. A contact lens packaging solution, which is a buffered saline which comprises:
   (1) a surfactant which is a poly(oxyethylene)-poly(oxybutylene) block copolymer; and
   (2) from about 0.1% to about 2% by weight of a lubricant which is a copolymer of N-vinylpyrrolidone and at least one amino-containing vinylic monomer, wherein the copolymer of N-vinylpyrrolidone and at least one amino-containing vinylic monomer has a molecular weight of at least 50,000 Daltons, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the contact lens packaging solution has a pH of from about 6.0 to about 8.0, an osmolality of from about 200 to about 450 mOsm/kg, and a viscosity of up to about 5.0 centipoises at 25° C., wherein the contact lens packaging solution is capable of providing a hydrogel contact lens immersed and autoclaved in the contact lens packaging solution in a package with a sustainable wettability, wherein the sustainable wettability of the hydrogel contact lens means that the hydrogel contact lens has a wearing-induced increase in water contact angle, designated "$\Delta \overline{WCA_{wearing}}$", of about 50% or less and/or a blinking-induced increase in water contact angle, designated "$\Delta \overline{WCA_{blinking}}$", of about 200% or less, wherein $$\Delta \overline{WCA_{wearing}} = \frac{\overline{WCA_{16H}} - \overline{WCA_{OOP}}}{\overline{WCA_{OOP}}}$$

in which $\overline{WCA_{OOP}}$ is the water contact angle of the hydrogel contact lens and is measured directly out of the package and $\overline{WCA_{16H}}$ is the water contact angle of the hydrogel contact lens and is measured after being transferred from the package to a container containing 1 mL of a phosphate buffered saline having a pH of 7.0 to 7.4 and then fully immersed and gently agitated in the phosphate buffered saline for 16 hours at 34° C., wherein $$\Delta \overline{WCA_{blinking}} = \frac{\overline{WCA_{10}} - \overline{WCA_0}}{\overline{WCA_0}}$$

in which $\overline{WCA_0}$ is the water contact angle of the hydrogel contact lens which is measured directly out of the package, and $\overline{WCA_{10}}$ is the water contact angle of the hydrogel contact lens which is measured after 10-cycles of wetting/drying treatment.

2. The contact lens packaging solution of claim 1, wherein the packaging solution comprises from about 0.001% to about 1% by weight, preferably from about 0.005% to about 0.5% by weight, and more preferably from about 0.01% to 0.1% by weight of the poly(oxyethylene)-poly(oxybutylene) block copolymer.

3. The contact lens packaging solution of claim 2, wherein the amino-containing vinylic monomer is dimethylaminoethylmethacrylate or dimethylaminoethylacrylate.

4. The contact lens packaging solution of claim 3, wherein the poly(oxyethylene)-poly(oxybutylene) block copolymer is a di-block copolymer of formula (I)

$$(EO)_m(BO)_n \qquad (I)$$

wherein m is an integer having an average value of 10 to 1000 and n is an integer having an average value of 5 to 1000, provided that the value of m/n is from about 2:1 to about 10:1.

5. The contact lens packaging solution of claim 4, wherein the di-block copolymer has formula (II)

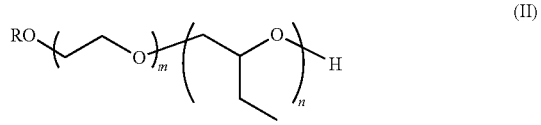

(II)

wherein R is selected from the group consisting of hydrogen, methyl, ethyl, propyl and butyl; m is an integer having an average value of 10 to 1000; and n is an integer having an average value of 5 to 1000, provided that the value of m/n is from about 2:1 to about 10:1.

6. The contact lens packaging solution of claim 5, wherein in formula (II) R is methyl; m has an average value of 45; and n has an average value of 10.

7. The contact lens packaging solution of claim 2, wherein the poly(oxyethylene)-poly(oxybutylene) block copolymer is a di-block copolymer of formula (I)

$$(EO)_m(BO)_n \qquad (I)$$

wherein m is an integer having an average value of 10 to 1000 and n is an integer having an average value of 5 to 1000, provided that the value of m/n is from about 2:1 to about 10:1.

8. The contact lens packaging solution of claim 7, wherein the di-block copolymer has formula (II)

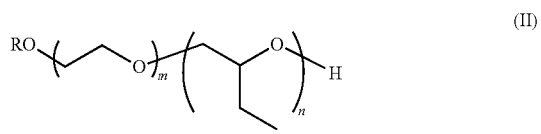

(II)

wherein R is selected from the group consisting of hydrogen, methyl, ethyl, propyl and butyl; m is an integer having an average value of 10 to 1000; and n is an integer having an average value of 5 to 1000, provided that the value of m/n is from about 2:1 to about 10:1.

9. The contact lens packaging solution of claim 8, wherein in formula (II) R is methyl; m has an average value of 45; and n has an average value of 10.

10. The contact lens packaging solution of claim 2, wherein the sustainable wettability of the hydrogel contact lens means that the hydrogel contact lens has a wearing-induced increase in water contact angle, designated "$\alpha WCA_{wearng}$", of about 30% or less.

11. The contact lens packaging solution of claim 10, wherein the sustainable wettability of the hydrogel contact lens means that the hydrogel contact lens also has a blinking-induced increase in water contact angle, designated "$\alpha WCA_{blinking}$", of about 150% or less.

12. The contact lens packaging solution of claim 2, wherein the sustainable wettability of the hydrogel contact lens means that the hydrogel contact lens has a blinking-induced increase in water contact angle, designated "$\alpha WCA_{blinking}$", of about 150% or less.

13. The contact lens packaging solution of claim 3, wherein the sustainable wettability of the hydrogel contact lens means that the hydrogel contact lens has a wearing-induced increase in water contact angle, designated "$\alpha WCA_{wearing}$", of about 30% or less.

14. The contact lens packaging solution of claim 13, wherein the sustainable wettability of the hydrogel contact lens means that the hydrogel contact lens also has a blinking-induced increase in water contact angle, designated "$\Delta WCA_{blinking}$", of about 150% or less.

15. The contact lens packaging solution of claim 3, wherein the sustainable wettability of the hydrogel contact lens means that the hydrogel contact lens has a blinking-induced increase in water contact angle, designated "$\alpha WCA_{blinking}$", of about 150% or less.

16. The contact lens packaging solution of claim 7, wherein the sustainable wettability of the hydrogel contact lens means that the hydrogel contact lens has a wearing-induced increase in water contact angle, designated "$\alpha WCA_{wearing}$", of about 30% or less.

17. The contact lens packaging solution of claim 16, wherein the sustainable wettability of the hydrogel contact lens means that the hydrogel contact lens also has a blinking-induced increase in water contact angle, designated "$\alpha WCA_{blinking}$", of about 150% or less.

18. The contact lens packaging solution of claim 7, wherein the sustainable wettability of the hydrogel contact lens means that the hydrogel contact lens has a blinking-induced increase in water contact angle, designated "$\alpha WCA_{blinking}$", of about 150% or less.

19. The contact lens packaging solution of claim 5, wherein the sustainable wettability of the hydrogel contact lens means that the hydrogel contact lens has a wearing-induced increase in water contact angle, designated "$\alpha WCA_{wearing}$", of about 30% or less.

20. The contact lens packaging solution of claim 19, wherein the sustainable wettability of the hydrogel contact lens means that the hydrogel contact lens also has a blinking-induced increase in water contact angle, designated "$\alpha WCA_{blinking}$", of about 150% or less.

* * * * *